US007655230B2

(12) United States Patent  
Bednar et al.

(10) Patent No.: US 7,655,230 B2
(45) Date of Patent: Feb. 2, 2010

(54) CO-ADMINISTRATION OF A TISSUE PLASMINOGEN ACTIVATOR, ANTI-CD11B ANTIBODY AND ANTI-CD18 ANTIBODY IN STROKE

(75) Inventors: Martin M. Bednar, South Burlington, VT (US); Cordell E. Gross, Williston, VT (US); Linda J. Gross, legal representative, Williston, VT (US); G. Roger Thomas, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 116 days.

(21) Appl. No.: 12/107,050

(22) Filed: Apr. 21, 2008

(65) Prior Publication Data

US 2009/0274689 A1   Nov. 5, 2009

Related U.S. Application Data

(63) Continuation of application No. 11/025,712, filed on Dec. 28, 2004, now Pat. No. 7,361,344, which is a continuation of application No. 10/404,286, filed on Mar. 31, 2003, now abandoned, which is a continuation of application No. 09/811,384, filed on Dec. 20, 2000, now abandoned, which is a continuation of application No. 09/251,652, filed on Feb. 17, 1999, now abandoned, which is a continuation-in-part of application No. 08/788,800, filed on Jan. 22, 1997, now Pat. No. 5,914,112.

(60) Provisional application No. 60/093,038, filed on Jan. 23, 1996.

(51) Int. Cl.
*A61K 39/395* (2006.01)
*A61K 38/49* (2006.01)
*C07K 16/28* (2006.01)

(52) U.S. Cl. ............. 424/144.1; 424/130.1; 424/133.1; 424/141.1; 424/153.1; 424/173.1; 424/94.2; 424/94.63; 424/94.64; 514/822; 530/387.1; 530/387.3; 530/388.1; 530/388.2; 530/388.22; 530/388.7

(58) Field of Classification Search ...................... None
See application file for complete search history.

(56) References Cited

U.S. PATENT DOCUMENTS

| | | |
|---|---|---|
| 4,797,277 A | 1/1989 | Arfors |
| 4,840,793 A | 6/1989 | Todd, III et al. |
| 4,935,234 A | 6/1990 | Todd, III et al. |
| 5,002,869 A | 3/1991 | Schlossman et al. |
| 5,071,964 A | 12/1991 | Dustin et al. |
| 5,147,637 A | 9/1992 | Wright et al. |
| 5,322,699 A | 6/1994 | Wright et al. |
| 5,914,112 A | 6/1999 | Bednar et al. |
| 7,361,344 B2 * | 4/2008 | Bednar et al. ............ 424/144.1 |

FOREIGN PATENT DOCUMENTS

| | | |
|---|---|---|
| AU | A-15518/88 | 11/1988 |
| CA | 2008368 | 6/1991 |
| EP | 289949 | 11/1988 |
| EP | 346078 | 12/1989 |
| EP | 379904 | 8/1990 |
| EP | 387668 | 9/1990 |
| EP | 438312 | 7/1991 |
| EP | 440351 | 8/1991 |
| WO | WO 90/10652 | 9/1990 |
| WO | WO 90/15076 | 12/1990 |
| WO | WO 91/16927 | 11/1991 |
| WO | WO 91/16928 | 11/1991 |
| WO | WO 91/18011 | 11/1991 |
| WO | WO 91/19511 | 12/1991 |
| WO | WO 92/22323 | 12/1992 |
| WO | WO 94/02175 | 2/1994 |
| WO | WO 94/04679 | 3/1994 |
| WO | WO 94/08620 | 4/1994 |
| WO | WO 94/12214 | 6/1994 |
| WO | WO 96/32478 | 10/1996 |
| WO | WO 97/26912 | 7/1997 |

OTHER PUBLICATIONS

Aversano et al., "A Chimeric IgG4 Monoclonal Antibody Directed Against CD18 Reduces Infarct Size in a Primate Model of Myocardial Ischemia and Reperfusion" *J. Amer. Col. Cardiology* 25 (3):781-788 (Mar. 1995).

Barron et al., "Use of reperfusion therapy for acute myocardial infarction in the United States: data from the National Registry of Myocardial Infarction 2" *Circulation* 97(12):1150-1156 (Mar. 31, 1998).

Bednar et al., "Comparison of Triphenyltetrazolium Dye with Light Microscopic Evaluation in a Rabbit Model of Acute Cerebral Ischaemia" *Neurological Research* 16:129-132 (Apr. 1994).

Bednar et al., "IB4, a Monoclonal Antibody Against the CD18 Adhesion Complex of Leukocytes, Attenuates Intracranial Hypertension in a Rabbit Stroke Model" *Stroke* (Abstract Only) 23(1):152 (1992).

Bednar et al., "IB4, a monoclonal antibody against the CD18 leukocyte adhesion protein, reduces intracranial pressure following thromboembolic stroke in the rabbit" *Neurological Res.* 18:171-175 (Apr. 1996).

Bednar et al., "The Role of Neutrophils and Platelets in a Rabbit Model of Thromboembolic Stroke" *Stroke* 22(1):44-50 (1991).

Bose et al., "Evolving Focal Cerebral Ischemia in Cats: Spatial Correlation of Nuclear Magnetic Resonance Imaging, Cerebral Blood Flow, Tetrazolium Staining, and Histopathology" *Stroke* 19(1):28-37 (Jan. 1988).

Bowes et al., "Monoclonal Antibodies Preventing Leukocyte Activation Reduce Experimental Neurologic Injury and Enhance Efficacy of Thrombolytic Therapy" *Neurology* 45:815-819 (1995).

(Continued)

*Primary Examiner*—Phillip Gambel
(74) *Attorney, Agent, or Firm*—David W. Evans; James A. Fox; Ginger R. Dreger

(57) ABSTRACT

A method for improving clinical outcome in focal ischemic stroke in a mammal by increasing cerebral blood flow and/or reducing infarct size is described which involves administering an effective amount of an anti-CD18 antibody to the mammal, in the absence of removal of the arterial obstruction.

18 Claims, 5 Drawing Sheets

OTHER PUBLICATIONS

Bowes et al., "Monoclonal Antibody to the ICAM-1 Adhesion Site Reduces Neurological Damage in a Rabbit Cerebral Embolism Stroke Model" *Experimental Neurology* 119(2):215-219 (1993).

Chen et al., "Anti-CD11b Monoclonal Antibody Reduce Ischemic Cell Damage After Transient Focal Cerebral Ischemia in Rat Anti-CD11b Monoclonal Antibody Reduces Ischemic Cell Damage After Transient Focal Cerebral Ischemia in Rat" *Ann. Neurol.* 35(4):458-463 (1994).

Chen et al., "Neutropenia Reduces The Volume of Cerebral Infarct After Transient Middle Cerebral Artery Occulsion in the Rat" *Neuroscience Research Communications* 11(2):93-99 (1992).

Chopp et al., "Anti-CD11b Monoclonal Antibody (1B6c) Reduces Infarct Size Resulting From Transient but Not Permanent Focal Ischemia in Rat" *Stroke* (Abstract Only) (19th International J), Stroke 25(1): p. 267, 1994.

Chopp et al., "Postischemic Administration of an Anti-MAC-1 Antibody Reduces Ischemic Cell Damage After Transient Middle Cerebral Artery Occlusion in Rats" *Stroke* 25(4):869-876 (1993).

Chopp et al., "The clot thickens—thrombolysis and combination therapies" *Acta Neurochirurgica* 73 (Suppl.):67-71 (1999).

Clark et al., "Reduction of Central Nervous System Ischemic Injury by Monoclonal Antibody to Intercellular Adhesion Molecule" *J. Neurosurg.* 75:623-627 (1991).

Clark et al., "Reduction of Central Nervous System Ischemic Injury in Rabbits Using Leukocyte Adhesion Antibody Treatment" *Stroke* 22(7):877-883 (Jul. 1991).

Clark et al., "Reperfusion Following Focal Stroke Hastens Inflammation and Resolution of Ischemic Injured Tissue" *Brain Research Bulletin* 35(4):387-392 (1994).

Danilenko et al., "A Novel Canine Leukointegrin, $\alpha_d\beta_2$, is Expressed by Specific Macrophage Subpopulations in Tissue and a Minor $CD8^+$ Lymphocyte Subpopulation in Peripheral Blood" *Journal of Immunology* 155:35-44 (1995).

del Zoppo et al., "Polymorphonuclear Leukocytes Occlude Capillaries Following Middle Cerebral Artery Occlusion and Reperfusion in Baboons" *Stroke* 22(10):1276-1283 (1991).

Desroches et al., "Regulation and Functional Involvement of Distinct Determinants of Leucocyte Function-Associated Antigen 1 (LFA-1) in T-Cell Activation In Vitro" *Scand. J. Immunol.* 33:277-286 (1991).

Eigenbrot et al., "X-Ray Structures of Fragments From Binding and Nonbinding Versions of a Humanized Anti-CD18 Antibody: Structural Indications of the Key Role of $V_H$ Residues 59 to 65" *Proteins: Structure, Function, and Genetics* 18:49-62 (1994).

Fekete et al., "Involvement of Lymphocyte Function-Associated Antigen-1 (LFA-1) But Not ICAM-1 in a Radioactive Leukocyte Cell-Mediated Immunity (LA-CMI) Assay" *J. Clin. Lab. Immunol.* 31:145-149 (1990).

Fisher et al., "The Penumbra, Therapeutic Time Window and Acute Ischaemic Stroke" *Bailliere's Clinical Neurology* 4(2):279-295 (Aug. 1995).

Garcia, "Effects of CD11b/18 Monocloan Antibody on Rats with Permanent Middle Cerebral Artery Occlusion" *Amer. J. Pathology* 148(1):241-248 (Jan. 1996).

Gross et al., "Delayed Tissue-Plasminogen Activator Therapy in a Rabbit Model of Thromoembolic Stroke" *Neurosurgery* 36(6):1172-1177 (1995).

Gross et al., "Transforming Growth Factor-β1 Reduces Infarct Size After Experimental Cerebral Ischemia in a Rabbit Model" *Stroke* 24(4):558-562 (Apr. 1993).

Hildreth & Hyman, "Production and characterization of Monoclonal Anti-CD18 Anti-Idiotype Antibodies" *Molecular Immunology* 26(12):1155-1167 (1989).

Hildreth et al., "A Human Lymphoctye-associated Antigen Involved in Cell-mediated Lympholysis" *European Journal of Immunology* 13:202-208 (1983).

Hutchings et al., "Transfer of Diabetes in Mice Prevented by Blockade of Adhesion-Promoting Receptor on Macrophages" *Nature* 348:639-642 (Dec. 13, 1990).

Jiang et al., "Anti-CD11b Monoclonal Antibody Reduces Ischemic Cell Damage After Transient (2h) But Not After Permanent MCA Occlusion in the Rat" *Neuroscience Research Communications* 15(2):85-93 (1994).

Jones et al., "Thresholds of Focal Cerebral Ischemia in Awake Monkeys" *Journal of Neurosurgery* 54:773-782 (Jun. 1981).

Kim et al., "Adhesive Glycoproteins CD11a are Upregulated in the Leukocytes from Patients with Ischemic Stroke and Transient Ischemic Attacks" *Journal of the Neurological Sciences* 128(1):45-50 (1995).

Kohut et al., "Reduction in Ischemic Brain Injury in Rabbits by the Anion Transport Inhibitor L-644, 711" *Stroke* 23(1):93-97 (Jan. 1992).

Kumar et al., "Recombinant soluble form of PSGL-1 accelerates thrombolysis and prevents reocclusion in a porcine model" *Circulation* 99(10):1363-1369 (Mar. 16, 1999).

Lew et al., "Complement depletion does not reduce brain injury in a rabbit model of thromboembolic stroke" *Brain Research Bulletin* 48(3):325-331 (Feb. 1999).

Lin et al., "Effect of Brain Edema on Infarct Volume in a Focal Cerebral Ischemia Model in Rats" *Stroke* 24(1):117-121 (Jan. 1993).

Lindsberg et al., "Antagonism of Neutrophil Adherence in the Deteriorating Stroke Model in Rabbits" *Journal of Neurosurgery* 82:269-277 (1995).

Link et al., "Neutrophil adhesion and activation during systemic thrombolysis in acute myocardial infarction" *Thrombosis Research* 91(4):183-190 (Aug. 15, 1998).

Matsuo et al., "Role of Cell Adhesion Molecules in Brain Injury After Transient Middle Cerebral Artery Occlusion in the Rat" *Brain Research* 656:344-352 (1994).

Mori et al., "Inhibition of Polymorphonuclear Leukoctye Adherence Suppresses No-Reflow After Focal Cerebral Ischemia in Baboons" *Stroke* 23(5):712-718 (May 1992).

Morioka et al., "Progressive Expression of Immunomolecules on Microglial Cells in Rat Dorsal Hippocampus Following Transient Forebrain Ischemia" *Acta Neuropatholigica*, Springer-Verlag vol. 83:149-157 (1992).

Perez et al., "Factors modifying protective effect of anti-CD18 antibodies on myocardial repefusion injury in dogs" *Amer. J. Physiology* (Part 2), Washington, D.C. 270(1):H53-H64 (1996).

Saez-Llorens et al., "Enhanced Attenuation of Meningeal Inflammation and Brain Edema by Concomitant Administration of Anti-CD18 Monoclonal Antibodies and Dexamethasone in Experimental Haemphilus meningitis" *Journal of Clin. Invest.* 88:2003-2009 (Dec. 1991).

Schroeter et al., "Local Immune Responses in the Rat Cerebral Cortex After Middle Cerebral Artery Occlusion" *Journal of Neuroimmunology*, Elsevier Science B.V. vol. 55(2):195-203 (1994).

Shiga et al., "Suppression of Ischemic Brain Edema in Rats by Depletion of Neutorphils" *Journal of Cerebral Blood Flow and Metabolism* (Abstract Only), Ginsberg et al., Supplement 2 edition, New York:Raven Press vol. 11(2):S486 (Jun. 1991).

Stringer et al., "Tissue plasminogen activator (tPA) inhibits interleukin-1 induced acute lung leak" *Free Radical Biology & Medicine* 25(2):184-188 (Jul. 15, 1998).

Takeshima et al., "Monoclonal Leukocyte Antibody Does Not Decrease the Injury of Transient Focal Cerebral Ischemia in Cats" *Stroke* 23(2):247-252 (Feb. 1992).

Vedder et al., "Inhibition of leukocyte adherence by anti-CD-18 monoclonal antibody attenuates reperfusion injury in the rabbit ear" *Proc. Natl. Acad. Sci. USA* 87:2643-2646 (Apr. 1990).

Wilson et al., "The Effect of the 21-Aminosteroid U74006F in a Rabbit Model of Thromboembolic Stroke" *Neurosurgery* 31(5):929-934 (Nov. 1992).

Young et al., "$H_2$ Clearance Measurement of Blood Flow: A Review of Technique and Polargraphic Principles" *Stroke* 11(5):552-564 (Sep. 1980).

Zhang et al., "Anti-Intercellular Adhesion Molecule-1 Antibody Reduces Ischemic Cell Damage After Transient But Not Permanent Middle Cerebral Artery Occlusion in the Wistar Rat" *Stroke* 26(8):1438-1442 (Aug. 1995).

Zhang et al., "Increased therapeutic efficacy with rt-PA and anti-CD18 antibody treatment of stroke in the rat" *Neurology* 52(2):273-279 (Jan. 15, 1999).

Zhang et al., "Postichemic Treatment (2-4h) with Anti-CD11b and Anti-CD18 Monoclonal Antibodies are Neuroprotective After Transient (2h) Focal Cerebral Ischemia in The Rat" *Brain Research*, Elsevier Science B.V. vol. 698:79-85 (1995).

Zhang et al., "Temporal Profile of Ischemic Tissue Damage, Neutrophil Response, and Vascular Plugging Following Permanent and Transient (2H) Middle Cerebral Artery Occlusion in the Rat" *Journal of the Neurological Sciences*, Elsevier Science B.V. vol. 125:3-10 (1994).

\* cited by examiner

| | |
|---|---|
| hIgG$_1$ | Sequence of human IgG1 CH1 domain |
| hIgG$_2$ | Sequence of human IgG2 CH1 domain |
| hIgG$_3$ | Sequence of human IgG3 CH1 domain |
| hIgG$_4$ | Sequence of human IgG4 CH1 domain |
| humκ | Sequence of human kappa CL domain |
| humλ | Sequence of human lambda CL domain |

```
                 114                      128                 139
                  |                        |                   |
hIgG1      A S T K G P S V F P L A P S S K S T S G G T A A L
hIgG2      A S T K G P S V F P L A P C S R S T S E S T A A L
hIgG3      A S T K G P S V F P L A P C S R S T S G G T A A L
hIgG4      A S T K G P S V F P L A P C S R S T S E S T A A L 108                      122                 131
                  |                        |                   |
humκ         R T V A A P S V F I F P P S D E Q L K S G T A S V
humλ         Q P K A A P S V T L F P P S S E E L Q A N K A T L

-------------------------------------------------------------------

Fabv1b     A S T K G P S V F P L A P S   P K N S SMISN T P A L
of interest                              P K N S SMISN T P most important                                    * * *    * hIgG1        G C L V K D Y F P E P V T V S W N S G A L T S
hIgG2        G C L V K D Y F P E P V T V S W N S G A L T S
hIgG3        G C L V K D Y F P E P V T V S W N S G A L T S
hIgG4        G C L V K D Y F P E P V T V S W N S G A L T S humκ           V C L L N N F Y P R E A K V Q W K V D N A L Q
humλ           V C L I S D F Y P G A V T V A W K A D S S P V

-------------------------------------------------------------------

Fabv1b       G C L V K D Y F P E P V T V S W N S G A L T S hIgG1        G V H T F P A V L Q S S G - - - L Y S L S S V
hIgG2        G V H T F P A V L Q S S G - - - L Y S L S S V
```

FIG. 4A

```
hIgG3         G V H T F P A V L Q S S G - - - L Y S L S S V
hIgG4         G V H T F P A V L Q S S G - - - L Y S L S S V
humκ            S G N S Q E S V T E Q D S K D S T Y S L S S T
humλ          K A G V E T T T P S K Q S N N - K Y A A S S Y
              ------------------------------------------------
Fabv1b        G V H T F P A V L Q S S G - - - L Y S L S S V
```

```
                       193             200 203
                        |               |   |
hIgG1         V T V P S S S L G T - Q T Y I C N V N H K P S
hIgG2         V T V P S S N F G T - Q T Y T C N V D H K P S
hIgG3         V T V P S S S L G T - Q T Y T C N V N H K P S
hIgG4         V T V P S S S L G T - K T Y T C N V D H K P S
                          181               190
                           |                 |
humκ          L T L S K A D Y E K H K V Y A C E V T H Q G L
humλ          L S L T P E Q W K S H R S Y S C Q V T H E G S
              ------------------------------------------------
Fabv1b        V T V P H Q S L G T - Q T Y I C N V N H K P S
of interest         H Q N L S D G K
                    _____
most important      *  *  *        *  *
```

```
hIgG1         N T K V D K R V - - -
hIgG2         N T K V D K T V - - -
hIgG3         N T K V D K R V - - -
hIgG4         N T K V D K R V - - - humκ          S S P V T K S F N R G E C
humλ          T V E K T V A P T E C S
              ------------------------------------------------
Fabv1b        N T K V D K R V - - -
```

FIG. 4B

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
        (A) LENGTH: 98 amino acids
        (B) TYPE: Amino Acid
        (D) TOPOLOGY: Linear (xi) SEQUENCE DESCRIPTION: SEQ ID NO: 1:

```
Ala Ser Thr Lys Gly Pro Ser Val Phe Pro Leu Ala Pro Ser Ser
 1               5                  10                  15

Lys Ser Thr Ser Gly Gly Thr Ala Ala Leu Gly Cys Leu Val Lys
                20                  25                  30

Asp Tyr Phe Pro Glu Pro Val Thr Val Ser Trp Asn Ser Gly Ala
                35                  40                  45

Leu Thr Ser Gly Val His Thr Phe Pro Ala Val Leu Gln Ser Ser
                50                  55                  60

Gly Leu Tyr Ser Leu Ser Ser Val Val Thr Val Pro Ser Ser Ser
                65                  70                  75

Leu Gly Thr Gln Thr Tyr Ile Cys Asn Val Asn His Lys Pro Ser
                80                  85                  90

Asn Thr Lys Val Asp Lys Arg Val
                95
```

(2) INFORMATION FOR SEQ ID NO: 2:

(i) SEQUENCE CHARACTERISTICS:
        (A) LENGTH: 98 amino acids
        (B) TYPE: Amino Acid
        (D) TOPOLOGY: Linear (xi) SEQUENCE DESCRIPTION: SEQ ID NO: 2:

```
Ala Ser Thr Lys Gly Pro Ser Val Phe Pro Leu Ala Pro Cys Ser
 1               5                  10                  15

Arg Ser Thr Ser Glu Ser Thr Ala Ala Leu Gly Cys Leu Val Lys
                20                  25                  30

Asp Tyr Phe Pro Glu Pro Val Thr Val Ser Trp Asn Ser Gly Ala
                35                  40                  45

Leu Thr Ser Gly Val His Thr Phe Pro Ala Val Leu Gln Ser Ser
                50                  55                  60

Gly Leu Tyr Ser Leu Ser Ser Val Val Thr Val Pro Ser Ser Asn
                65                  70                  75
```

```
Phe Gly Thr Gln Thr Tyr Thr Cys Asn Val Asp His Lys Pro Ser
             80                  85                  90

Asn Thr Lys Val Asp Lys Thr Val
             95
```

(2) INFORMATION FOR SEQ ID NO: 3:

(i) SEQUENCE CHARACTERISTICS:
        (A) LENGTH: 98 amino acids
        (B) TYPE: Amino Acid
        (D) TOPOLOGY: Linear (xi) SEQUENCE DESCRIPTION: SEQ ID NO: 3:

```
Ala Ser Thr Lys Gly Pro Ser Val Phe Pro Leu Ala Pro Cys Ser
 1               5                  10                  15

Arg Ser Thr Ser Gly Gly Thr Ala Ala Leu Gly Cys Leu Val Lys
             20                  25                  30

Asp Tyr Phe Pro Glu Pro Val Thr Val Ser Trp Asn Ser Gly Ala
             35                  40                  45

Leu Thr Ser Gly Val His Thr Phe Pro Ala Val Leu Gln Ser Ser
             50                  55                  60

Gly Leu Tyr Ser Leu Ser Ser Val Val Thr Val Pro Ser Ser Ser
             65                  70                  75

Leu Gly Thr Gln Thr Tyr Thr Cys Asn Val Asn His Lys Pro Ser
             80                  85                  90

Asn Thr Lys Val Asp Lys Arg Val
             95
```

(2) INFORMATION FOR SEQ ID NO: 4:

(i) SEQUENCE CHARACTERISTICS:
        (A) LENGTH: 98 amino acids
        (B) TYPE: Amino Acid
        (D) TOPOLOGY: Linear (xi) SEQUENCE DESCRIPTION: SEQ ID NO: 4:

```
Ala Ser Thr Lys Gly Pro Ser Val Phe Pro Leu Ala Pro Cys Ser
 1               5                  10                  15

Arg Ser Thr Ser Glu Ser Thr Ala Ala Leu Gly Cys Leu Val Lys
             20                  25                  30

Asp Tyr Phe Pro Glu Pro Val Thr Val Ser Trp Asn Ser Gly Ala
             35                  40                  45

Leu Thr Ser Gly Val His Thr Phe Pro Ala Val Leu Gln Ser Ser
             50                  55                  60

Gly Leu Tyr Ser Leu Ser Ser Val Val Thr Val Pro Ser Ser Ser
             65                  70                  75

Leu Gly Thr Lys Thr Tyr Thr Cys Asn Val Asp His Lys Pro Ser
             80                  85                  90

Asn Thr Lys Val Asp Lys Arg Val
             95
```

(2) INFORMATION FOR SEQ ID NO: 5:

(i) SEQUENCE CHARACTERISTICS:
        (A) LENGTH: 107 amino acids
        (B) TYPE: Amino Acid
        (D) TOPOLOGY: Linear (xi) SEQUENCE DESCRIPTION: SEQ ID NO: 5:

```
Arg Thr Val Ala Ala Pro Ser Val Phe Ile Phe Pro Pro Ser Asp
```

```
              1               5              10              15

Glu Gln Leu Lys Ser Gly Thr Ala Ser Val Val Cys Leu Leu Asn
                 20                  25                  30

Asn Phe Tyr Pro Arg Glu Ala Lys Val Gln Trp Lys Val Asp Asn
                 35                  40                  45

Ala Leu Gln Ser Gly Asn Ser Gln Glu Ser Val Thr Glu Gln Asp
                 50                  55                  60

Ser Lys Asp Ser Thr Tyr Ser Leu Ser Ser Thr Leu Thr Leu Ser
                 65                  70                  75

Lys Ala Asp Tyr Glu Lys His Lys Val Tyr Ala Cys Glu Val Thr
                 80                  85                  90

His Gln Gly Leu Ser Ser Pro Val Thr Lys Ser Phe Asn Arg Gly
                 95                 100                 105

Glu Cys (2) INFORMATION FOR SEQ ID NO: 6:

(i) SEQUENCE CHARACTERISTICS:
         (A) LENGTH: 105 amino acids
         (B) TYPE: Amino Acid
         (D) TOPOLOGY: Linear (xi) SEQUENCE DESCRIPTION: SEQ ID NO: 6:

Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser
                 20                  25                  30

Asp Phe Tyr Pro Gly Ala Val Thr Val Ala Trp Lys Ala Asp Ser
                 35                  40                  45

Ser Pro Val Lys Ala Gly Val Glu Thr Thr Thr Pro Ser Lys Gln
                 50                  55                  60

Ser Asn Asn Lys Tyr Ala Ala Ser Ser Tyr Leu Ser Leu Thr Pro
                 65                  70                  75

Glu Gln Trp Lys Ser His Arg Ser Tyr Ser Cys Gln Val Thr His
                 80                  85                  90

Glu Gly Ser Thr Val Glu Lys Thr Val Ala Pro Thr Glu Cys Ser
                 95                 100                 105

(2) INFORMATION FOR SEQ ID NO: 7:

(i) SEQUENCE CHARACTERISTICS:
         (A) LENGTH: 100 amino acids
         (B) TYPE: Amino Acid
         (D) TOPOLOGY: Linear (xi) SEQUENCE DESCRIPTION: SEQ ID NO: 7:

Ala Ser Thr Lys Gly Pro Ser Val Phe Pro Leu Ala Pro Ser Pro
 1               5                  10                  15

Lys Asn Ser Ser Met Ile Ser Asn Thr Pro Ala Leu Gly Cys Leu
                 20                  25                  30

Val Lys Asp Tyr Phe Pro Glu Pro Val Thr Val Ser Trp Asn Ser
                 35                  40                  45

Gly Ala Leu Thr Ser Gly Val His Thr Phe Pro Ala Val Leu Gln
                 50                  55                  60

Ser Ser Gly Leu Tyr Ser Leu Ser Ser Val Val Thr Val Pro His
                 65                  70                  75

Gln Ser Leu Gly Thr Gln Thr Tyr Ile Cys Asn Val Asn His Lys
```

-continued

```
                    80                  85                  90
Pro Ser Asn Thr Lys Val Asp Lys Arg Val
                    95                 100
```

(2) INFORMATION FOR SEQ ID NO: 8:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO: 8:

```
Pro Lys Asn Ser Ser Met Ile Ser Asn Thr Pro
 1               5                  10
```

(2) INFORMATION FOR SEQ ID NO: 9:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO: 9:

```
His Gln Asn Leu Ser Asp Gly Lys
 1               5
```

(2) INFORMATION FOR SEQ ID NO: 10:

(i) SEQUENCE CHARACTERISTICS:
        (A) LENGTH: 232 amino acids
        (B) TYPE: Amino Acid
        (D) TOPOLOGY: Linear (xi) SEQUENCE DESCRIPTION: SEQ ID NO: 10:

```
Glu Val Gln Leu Val Glu Ser Gly Gly Gly Leu Val Gln Pro Gly
 1               5                  10                  15

Gly Ser Leu Arg Leu Ser Cys Ala Thr Ser Gly Tyr Thr Phe Thr
                20                  25                  30

Glu Tyr Thr Met His Trp Met Arg Gln Ala Pro Gly Lys Gly Leu
                35                  40                  45

Glu Trp Val Ala Gly Ile Asn Pro Lys Asn Gly Gly Thr Ser His
                50                  55                  60

Asn Gln Arg Phe Met Asp Arg Phe Thr Ile Ser Val Asp Lys Ser
                65                  70                  75

Thr Ser Thr Ala Tyr Met Gln Met Asn Ser Leu Arg Ala Glu Asp
                80                  85                  90

Thr Ala Val Tyr Tyr Cys Ala Arg Trp Arg Gly Leu Asn Tyr Gly
                95                 100                 105

Phe Asp Val Arg Tyr Phe Asp Val Trp Gly Gln Gly Thr Leu Val
                110                 115                 120

Thr Val Ser Ser Ala Ser Thr Lys Gly Pro Ser Val Phe Pro Leu
                125                 130                 135

Ala Pro Ser Ser Lys Ser Thr Ser Gly Gly Thr Ala Ala Leu Gly
                140                 145                 150

Cys Leu Val Lys Asp Tyr Phe Pro Glu Pro Val Thr Val Ser Trp
                155                 160                 165

Asn Ser Gly Ala Leu Thr Ser Gly Val His Thr Phe Pro Ala Val
                170                 175                 180

Leu Gln Ser Ser Gly Leu Tyr Ser Leu Ser Ser Val Val Thr Val
                185                 190                 195
```

```
Pro Ser Ser Ser Leu Gly Thr Gln Thr Tyr Ile Cys Asn Val Asn
            200                 205                 210

His Lys Pro Ser Asn Thr Lys Val Asp Lys Lys Val Glu Pro Lys
            215                 220                 225

Ser Cys Asp Lys Thr His Thr
            230
```

(2) INFORMATION FOR SEQ ID NO: 11:

(i) SEQUENCE CHARACTERISTICS:
        (A) LENGTH: 214 amino acids
        (B) TYPE: Amino Acid
        (D) TOPOLOGY: Linear (xi) SEQUENCE DESCRIPTION: SEQ ID NO: 11:

```
Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Ile Asn
            20                  25                  30

Asn Tyr Leu Asn Trp Tyr Gln Gln Lys Pro Gly Lys Ala Pro Lys
            35                  40                  45

Leu Leu Ile Tyr Tyr Thr Ser Thr Leu His Ser Gly Val Pro Ser
            50                  55                  60

Arg Phe Ser Gly Ser Gly Ser Gly Thr Asp Tyr Thr Leu Thr Ile
            65                  70                  75

Ser Ser Leu Gln Pro Glu Asp Phe Ala Thr Tyr Tyr Cys Gln Gln
            80                  85                  90

Gly Asn Thr Leu Pro Pro Thr Phe Gly Gln Gly Thr Lys Val Glu
            95                  100                 105

Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
            125                 130                 135

Leu Asn Asn Phe Tyr Pro Arg Glu Ala Lys Val Gln Trp Lys Val
            140                 145                 150

Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
            185                 190                 195

Val Thr His Gln Gly Leu Ser Ser Pro Val Thr Lys Ser Phe Asn
            200                 205                 210

Arg Gly Glu Cys
```

(2) INFORMATION FOR SEQ ID NO: 12:

(i) SEQUENCE CHARACTERISTICS:
        (A) LENGTH: 450 amino acids
        (B) TYPE: Amino Acid
        (D) TOPOLOGY: Linear (xi) SEQUENCE DESCRIPTION: SEQ ID NO: 12:

```
Glu Val Gln Leu Val Glu Ser Gly Gly Gly Leu Val Gln Pro Gly
 1               5                  10                  15

Gly Ser Leu Arg Leu Ser Cys Ala Thr Ser Gly Tyr Thr Phe Thr
            20                  25                  30
```

-continued

```
Glu Tyr Thr Met His Trp Met Arg Gln Ala Pro Gly Lys Gly Leu
             35                  40                  45

Glu Trp Val Ala Gly Ile Asn Pro Lys Asn Gly Gly Thr Ser His
         50                  55                  60

Asn Gln Arg Phe Met Asp Arg Phe Thr Ile Ser Val Asp Lys Ser
     65                  70                  75

Thr Ser Thr Ala Tyr Met Gln Met Asn Ser Leu Arg Ala Glu Asp
 80                  85                  90

Thr Ala Val Tyr Tyr Cys Ala Arg Trp Arg Gly Leu Asn Tyr Gly
             95                 100                 105

Phe Asp Val Arg Tyr Phe Asp Val Trp Gly Gln Gly Thr Leu Val
        110                 115                 120

Thr Val Ser Ser Ala Ser Thr Lys Gly Pro Ser Val Phe Pro Leu
    125                 130                 135

Ala Pro Cys Ser Arg Ser Thr Ser Glu Ser Thr Ala Ala Leu Gly
140                 145                 150

Cys Leu Val Lys Asp Tyr Phe Pro Glu Pro Val Thr Val Ser Trp
            155                 160                 165

Asn Ser Gly Ala Leu Thr Ser Gly Val His Thr Phe Pro Ala Val
        170                 175                 180

Leu Gln Ser Ser Gly Leu Tyr Ser Leu Ser Ser Val Val Thr Val
    185                 190                 195

Thr Ser Ser Asn Phe Gly Thr Gln Thr Tyr Thr Cys Asn Val Asp
200                 205                 210

His Lys Pro Ser Asn Thr Lys Val Asp Lys Thr Val Glu Arg Lys
            215                 220                 225

Cys Cys Val Glu Cys Pro Pro Cys Pro Ala Pro Pro Val Ala Gly
        230                 235                 240

Pro Ser Val Phe Leu Phe Pro Pro Lys Pro Lys Asp Thr Leu Met
    245                 250                 255

Ile Ser Arg Thr Pro Glu Val Thr Cys Val Val Val Asp Val Ser
260                 265                 270

His Glu Asp Pro Glu Val Gln Phe Asn Trp Tyr Val Asp Gly Met
            275                 280                 285

Glu Val His Asn Ala Lys Thr Lys Pro Arg Glu Glu Gln Phe Asn
        290                 295                 300

Ser Thr Phe Arg Val Val Ser Val Leu Thr Val Val His Gln Asp
    305                 310                 315

Trp Leu Asn Gly Lys Glu Tyr Lys Cys Lys Val Ser Asn Lys Gly
320                 325                 330

Leu Pro Ala Pro Ile Glu Lys Thr Ile Ser Lys Thr Lys Gly Gln
            335                 340                 345

Pro Arg Glu Pro Gln Val Tyr Thr Leu Pro Pro Ser Arg Glu Glu
        350                 355                 360

Met Thr Lys Asn Gln Val Ser Leu Thr Cys Leu Val Lys Gly Phe
    365                 370                 375

Tyr Pro Ser Asp Ile Ala Val Glu Trp Glu Ser Asn Gly Gln Pro
380                 385                 390

Glu Asn Asn Tyr Lys Thr Thr Pro Pro Met Leu Asp Ser Asp Gly
            395                 400                 405

Ser Phe Phe Leu Tyr Ser Lys Leu Thr Val Asp Lys Ser Arg Trp
        410                 415                 420
```

```
                              -continued

Gln Gln Gly Asn Val Phe Ser Cys Ser Val Met His Glu Ala Leu
            425                 430                 435

His Asn His Tyr Thr Gln Lys Ser Leu Ser Leu Ser Pro Gly Lys
            440                 445                 450

(2) INFORMATION FOR SEQ ID NO: 13:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO: 13:

His Gln Ser Leu Gly Thr Gln
 1               5

(2) INFORMATION FOR SEQ ID NO: 14:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO: 14:

His Gln Asn Ile Ser Asp Gly Lys
 1               5

(2) INFORMATION FOR SEQ ID NO: 15:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO: 15:

Val Ile Ser Ser His Leu Gly Gln
 1               5
```

CO-ADMINISTRATION OF A TISSUE PLASMINOGEN ACTIVATOR, ANTI-CD11B ANTIBODY AND ANTI-CD18 ANTIBODY IN STROKE

RELATED APPLICATION

This application is a continuation of application Ser. No. 11/025,712, filed Dec. 28, 2004, now U.S. Pat. No. 7,361,344, which is a continuation of application Ser. No. 10/404,286, filed Mar. 31, 2003, abandoned, which is a continuation of application Ser. No. 09/811,384, filed Dec. 20, 2000, abandoned, claiming priority under 35 U.S.C. §120 to non-provisional application U.S. Ser. No. 09/251,652, filed Feb. 17, 1999, abandoned, which is a continuation-in-part application claiming priority under 35 U.S.C. §120 to non-provisional application U.S. Ser. No. 08/788,800, filed Jan. 22, 1997, now U.S. Pat. No. 5,914,112, which claims priority under 35 U.S.C. §119(e) to provisional application U.S. Ser. No. 60/093,038, filed Jan. 23, 1996, (which was converted from non-provisional application U.S. Ser. No. 08/589,982 by petition), the entire disclosures of which non-provisional and provisional applications are incorporated herein by reference.

This invention was made with United States government support under grant NS31008 and NS28708 awarded by the National Institutes of Health. The United States government has certain rights in the invention.

BACKGROUND OF THE INVENTION

1. Field of the Invention

This invention relates generally to the use of anti-CD18 antibodies for treating stroke. In particular, it relates to the use of anti-CD18 antibodies for improving clinical outcome by increasing cerebral blood flow and/or reducing infarct size in focal ischemic stroke caused by obstruction of a main cerebral artery.

2. Description of Related Art

Stroke is a general term for acute brain damage resulting from disease of blood vessels. This presents a serious problem to society, with about 500,000 people dying from or becoming permanently disabled by stroke in the United States each year. Stroke can be classified into two main categories: hemorrhagic stroke (resulting from leakage of blood outside of the normal blood vessels) and ischemic stroke (cerebral ischemia due to lack of blood supply); this application is primarily concerned with the latter.

The three main mechanisms of ischemic stroke are thrombosis, embolism and systemic hypoperfusion (with resultant ischemia and hypoxia). In each of these types of stroke, the area of the brain that dies as a result of the lack of blood supply thereto is called an infarct. Obstruction of a cerebral artery resulting from a thrombus which has built up on the wall of a brain artery is generally called cerebral thrombosis. In cerebral embolism, the occlusive material blocking the cerebral artery arises downstream in the circulation (e.g. an embolus is carried to the cerebral artery from the heart). Because it is difficult to discern whether a stroke is caused by thrombosis or embolism, the term thromboembolism is used to cover both these types of stroke. Systemic hyperfusion may arise as a consequence of decreased blood levels, reduced hematocrit, low blood pressure or inability of the heart to pump blood adequately.

When symptoms of stroke last less than 24 hours and the patient recovers completely, the patient is said to have undergone a transient ischemic attack (TIA). The symptoms of TIA are a temporary impairment of speech, vision, sensation or movement. Because a TIA is often thought to be a prelude to full-scale stroke, patients having suffered a TIA are candidates for prophylactic stroke therapy with anticoagulation agents (e.g., coumarin and heparin) or antiplatelet agents (such as aspirin and ticlopidine) for example.

Thrombotytic agents, such as tissue plasminogen activator (t-PA), have been used in the treatment of thromboembolic stroke. These molecules function by lysing the thrombus causing the ischemia. Such drugs are believed to be most useful if administered as soon as possible after acute stroke (preferably within 3 hours) in order to at least partially restore cerebral blood flow in the ischemic region and to sustain neuronal viability. In that such drugs exacerbate bleeding, their use In hemorrhagic stroke is contra-indicated.

A family of adhesion glycoproteins present on leukocytes is called the integrin family. This integrin family includes LFA-1 (CD11a/CD18), Mac-1 (CD11b/CD18) and p 150,95 (CD11c/CD18). A further member of this family CD11d/CD18 has recently been reported. Danilenko et al., *J. Immunol.* 155:35-44 (1995). Each of these heterodimers has a unique α-chain (CD11a, b, c or d) and the invariant β-chain (CD18). CD18 integrins located on leukocytes may bind to intercellular adhesion molecule-1 (ICAM-1) which is expressed on vascular endothelium and other cells, thereby mediating leukocyte adhesion and transendothelial migration.

It has been noted that CD11a and CD18 are upregulated in leukocytes from patients who have undergone ischemic stroke or a TIA. Kim et al., *J. Neurolog. Sci.* 128(1):45-50 (1995). Schroeter et al., *J. Neuroimmunology* 55(2):195-203 (1994) found that increased expression of ICAM-1 on vessels and leukocytes occurred following cerebral ischemia induced by permanent occlusion of the middle cerebral artery (MCA) in the rat.

The role of cell adhesion molecules in brain injury following transient MCA occlusion in the rat has been studied (Matsuo et al., *Brain Research* 656:344-352 (1994)). Matsuo et al. inserted a nylon thread from the lumen of the external carotid artery (ECA) to that of the right internal carotid artery (ICA) in order to occlude the origin of the right MCA. The occlusion was transient; after 1 hour, the nylon thread was removed to allow complete reperfusion of the ischemic area via the right common carotid artery (CCA). Anti-CD11a (WT1), anti-CD18 (WT3) and anti-ICAM-1 (1A29) antibodies were administered before ischemia and immediately after reperfusion. These researchers found that treatment with individual antibodies against cell adhesion molecules reduced edema formation, infarct size and neutrophil accumulation following reperfusion.

Others have investigated the effects of antibodies against cell adhesion molecules in such transient stroke models. Zhang et al., *Brain Research* 698:79-85 (1995) studied the effects of anti-CD11b and anti-CD18 monoclonal antibodies in ischemia/reperfusion injury, wherein the antibodies were administered upon and after transient MCA occlusion (the origin of the MCA was transiently blocked with a surgical nylon filament). Mori et al., *Stroke* 23(5): 712-718 (1992) studied the effects of the anti-CD18 IB4 antibody in their baboon model of reversible MCA occlusion. In this model, arterial obstruction was achieved by inflating an extrinsic MCA balloon to 100 μl. Reperfusion occurred following balloon deflation. See, also, Chopp et al., *Stroke* 25(4):869-876 (1994) and Chen et al., *Annals of Neurology* 35(4): 458-463 (1994) concerning an anti-CD11b antibody in a transient cerebral ischemia model. Chopp et al., and Chen et al., advanced a surgical nylon suture into the ICA to block the origin of the MCA. Reperfusion was accomplished by withdrawing the suture until the tip cleared the ICA lumen.

Takeshima et al., *Stroke,* 23(2):247-252 (1992) found that the anti-CD18 antibody 60.3 did not afford protection from severe focal ischemia and reperfusion in a transient focal cerebral ischemia model in cats. Takeshima et al. used a microvascular clip to occlude the MCA and occluded CCAs by tightening previously placed ligatures.

Lindsberg et al. *J. Neurosurg.* 82:269-277 (1995) subjected rabbits to severe spinal cord ischemia (by inflating the balloon of a catheter tip which had been introduced in the abdominal aorta) followed by 30 minutes of reperfusion at which time either: (1) vehicle, (2) anti-CD18 antibody, or (3) anti-CD18 antibody and platelet-activating factor (PAF) antagonist were administered to the animals. Recovery of motor function was improved by the anti-CD18 antibody, but no further improvement was induced by the PAF antagonist.

It has been observed that while an anti-CD18 antibody reduced neurologic deficits in the reversible spinal cord model (involving a snare ligature occluding device), it was unable to do so in an irreversible microsphere model. Clark et al., *Stroke* 22(7): 877-883 (1991). Clark et al., conclude that leukocytes potentiate their effect in central nervous system injury via reperfusion injury. With respect to anti-CD11b antibodies, Chopp et al., *Stroke* 25(1):267 (1994) report that benefit from administration of such antibodies was observed under conditions of transient, but not permanent, MCA occlusion in rats. See, also, Jiang et al., *Neuroscience Research Communications* 15(2):85-93 (1994). Clark et al., *J. Neurosurg* 75(4):623-627 (1991) also observe that while anti-ICAM-1 produced a significant reduction in neurological deficits in the reversible spinal cord ischemia model, such therapeutic benefit was not seen in the irreversible brain ischemia model. Similar findings in relation to anti-ICAM-1 antibodies have also been reported by Zhang et al., *Stroke* 26(8):1438-1442 (1995).

Bowes et al., *Neurology* 45:815-819 (1995) evaluated the ability of monoclonal antibodies directed against ICAM-1 and CD18 to enhance the efficacy of thrombolysis in a rabbit cerebral embolism stroke model. In this model, numerous small blood clots (formed by fragmenting a clot with a tissue homogenizer) were injected into the rabbit's carotid circulation in order to achieve embolization. Neurologic function in each animal was evaluated 18 hours following embolization on a three point scale: (1) normal activity; (2) abnormal activity; or (3) death. The amount of clot necessary to produce permanent neurologic damage in 50% of the rabbits ($ED_{50}$) was determined for each treatment group. Bowes et al., found that when administration of anti-CD18 or anti-ICAM-1 was delayed until 15 or 30 minutes after embolization, a statistically significant improvement in neurologic function was not observed. See also Bowes et al., *Experimental Neurology* 119(2):215-219 (1993) in relation to earlier work by this group regarding anti-ICAM-1 and t-PA in their rabbit cerebral embolism stroke model.

Bednar et al., *Stroke* 23(1):152 (1992) describe a rabbit model of thromboembolic stroke wherein the arterial occlusion (an autologous blood clot delivered to the anterior cerebral circulation) is not removed during the experiment. Rabbits received either anti-CD18 antibody IB4 (1 mg/kg), or vehicle, 30 minutes following the thromboembolic event. Following embolization, the animals were studied for a total of 4 hours, including an initial 45 minutes of systemic hypotension. No statistically significant difference in cerebral blood flow (CBF) or infarct size between IB4 and vehicle treated animals was seen. However, IB4 did attenuate intracranial hypertension in this model.

It is an object of the present invention to provide a method for improving clinical outcome in acute ischemic stroke by increasing cerebral blood flow and/or reducing infarct size. Furthermore, it is an object of the invention to provide an alternative to thrombolytic therapy for treating thromboembolic stroke, particularly where thrombolytic therapy has been unsuccessful or is contra-indicated, as is the case where the patient to be treated is taking aspirin, or where the time delay from the onset of stroke to diagnosis is such that thrombolytic therapy is not recommended. Other objects will be apparent from the description which follows.

SUMMARY OF THE INVENTION

This application is based on the unexpected finding that anti-CD18 antibodies can lead to a significant increase in cerebral blood flow and/or reduction in brain infarct size in focal ischemic stroke, in the absence of removal of the arterial obstruction.

Accordingly, the invention provides a method for treating stroke in a mammal (e.g. focal ischemic stroke caused by obstruction of a main cerebral artery) which comprises the step of administering an amount of CD18 antagonist and/or CD11b antagonist to the mammal which is effective for increasing cerebral blood flow and/or reducing cerebral infarct size in the mammal. In the method, the arterial obstruction (generally a single thrombus or embolus) is not removed by mechanical means (e.g. by surgically removing the obstruction) or chemical means (e.g. by using a thrombolytic agent to dissolve the arterial obstruction). Furthermore, the recipient of the CD18 or CD11b antagonist is not subjected to extraneous systemic hypotension (e.g., via controlled exsanguination) during the method as was the case in Bednar et al., *Stroke* 23(1):152 (1992).

Preferably the antagonist is an anti-CD18 antibody, such as a humanized F(ab')$_2$ fragment. Conveniently, the antagonist is administered to the mammal in the form of a pharmaceutically acceptable formulation, such as those elaborated in more detail herein.

The preferred mode of administration of the antagonist is by bolus intravenous dosage. In certain embodiments of the invention, the antagonist may be administered at least once a time between about 15 minutes to about 20 hours and preferably between about 30 minutes to about 12 hours from the onset of focal ischemic stroke. Single or multiple dosages may be given. Alternatively, or in addition, the antagonist may be administered via continuous infusion.

In another aspect, the invention relates to a method for treating ischemic stroke caused by systemic hypoperfusion or hypoxia in a mammal (e.g. resulting from cardiac arrest or drowning) which comprises the step of administering a therapeutically effective amount of CD11b antagonist and/or CD18 antagonist to the mammal. The preferred antagonist for use in this method is an anti-CD18 antibody. Preferably, the method results in an increase in cerebral blood flow and a decrease in infarct size resulting from the systemic hypoperfusion.

In yet another embodiment, the invention provides a method for increasing cerebral blood flow and/or reducing infarct size in focal ischemic stroke caused by obstruction of a main cerebral artery which comprises the step of administering a therapeutically effective amount of CD18 and/or CD11b antagonist to the mammal at least once at a time more than 15 mins (e.g. more than 30 mins) and preferably less than 24 hours from the onset of focal ischemic stroke in the mammal. In the method, the mammal being treated is not subjected to extraneous systemic hypotension as described in Bednar et al., Stroke 23(1):152 (1992). Preferably the antagonist is an anti-CD18 antibody which is administered at least once at a time between about 30 minutes to about 12 hours from the onset of focal ischemic stroke.

According to the method of the previous paragraph, a therapeutically effective amount of a thrombolytic agent (such as t-PA) may be co-administered to the mammal either before, after, or simultaneously with, the CD11b or CD18 antagonist. Preferably, the antagonist is administered to the mammal prior to administration of the thrombolytic agent. According to this method, the thrombolytic agent may be administered to the mammal more than about 3 hours after the onset of ischemic stroke (e.g., at least once within about 3-8 hours and preferably within about 3-5 hours from the onset of stroke). The thrombolytic agent may be administered by one or more bolus doses or by continuous infusion, for example.

The invention also provides articles of manufacture and kits for use in the above methods.

BRIEF DESCRIPTION OF THE DRAWINGS

FIGS. 4A-B depict an alignment of the relevant portions of the consensus amino acid sequences of the human $IgG_1$ CH1 domain (SEQ ID NO: 1), the human $IgG_2$CH1 domain (SEQ ID NO: 2), the human $IgG_3$ CH1 domain (SEQ ID NO: 3), the human $IgG_4$ CH1 domain (SEQ ID NO: 4), the human $\kappa\ C_L$ domain (SEQ ID NO: 5), and the human $\lambda\ C_L$ domain (SEQ ID NO: 6), in alignment with the Fabv1b variant derived from an anti-CD18 antibody (SEQ ID NO: 7). In FIGS. 4A-B, amino acid residues and/or positions of interest and of most importance for use as salvage receptor binding epitopes within the sequence of Fabv1b (i.e., SEQ ID NOS: 8 and 9) are designated by underlining and asterisks, respectively.

DETAILED DESCRIPTION OF THE PREFERRED EMBODIMENTS

1. Definitions

Figure 1:
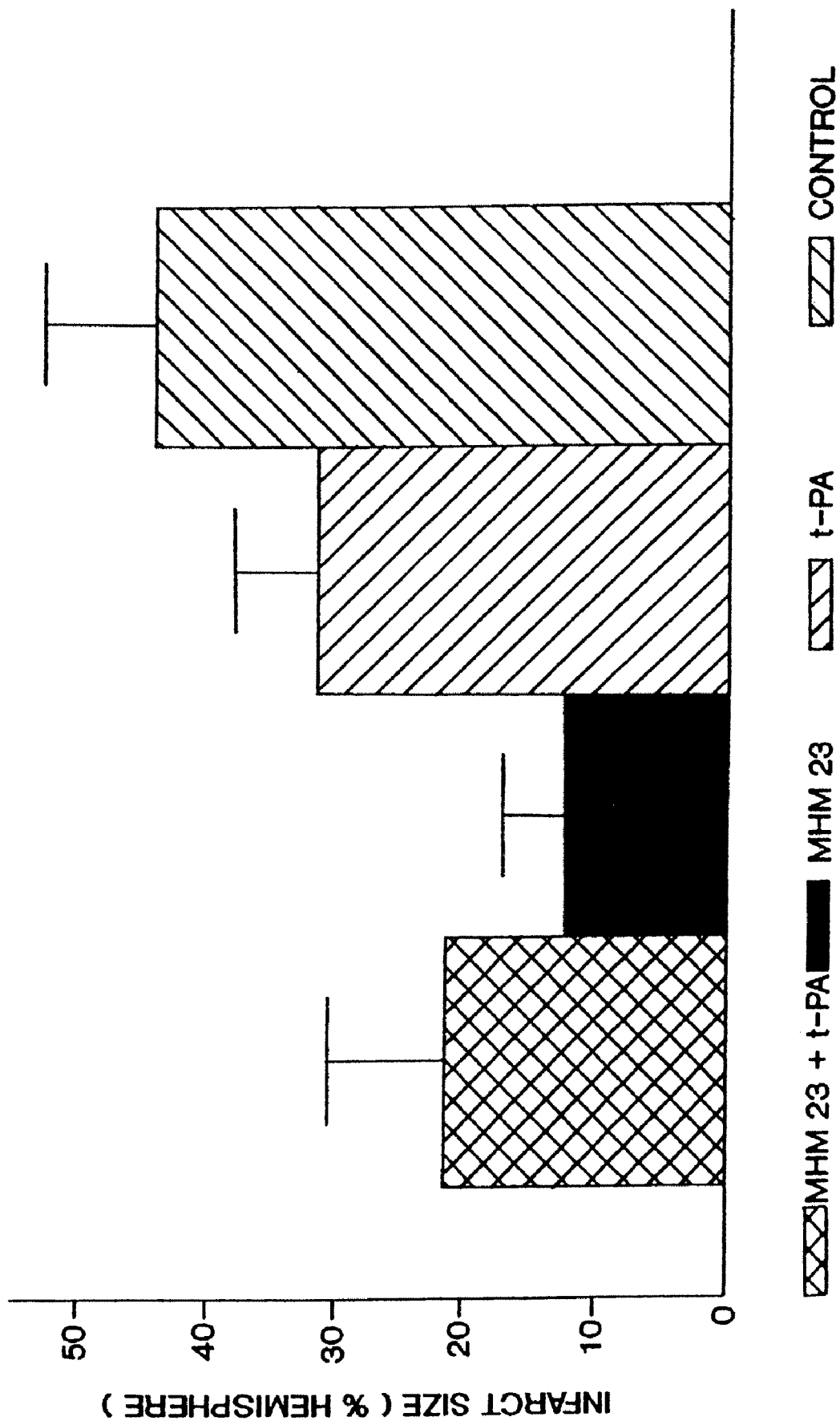
FIG. 1 is a bar graph depicting brain infarct size (% hemisphere infarcted) in embolized rabbits following treatment with MHM23 (anti-CD18) and t-PA (n=5); MHM23 alone (n=5); t-PA alone (n=10) or saline solution control (n=10) as described in Example 1 (mean+/−standard error of the mean).

"Focal ischemic stroke" is defined herein as damage to the brain caused by interruption of the blood supply to a region thereof. The focal ischemic stroke of interest herein is generally caused by obstruction of any one or more of the "main cerebral arteries" (e.g. middle cerebral artery, anterior cerebral artery, posterior cerebral artery, internal carotid artery, vertebral artery or basilar artery), as opposed to secondary arteries or arterioles. The "arterial obstruction" is generally a single embolus or thrombus. Hence, focal ischemic stroke as defined herein is distinguished from the cerebral embolism stroke model of Bowes et al., Neurology 45:815-819 (1995) in which a plurality of clot particles occlude secondary arteries or arterioles.

The expression "in the absence of removal of the arterial obstruction" when used throughout this application means that the arterial obstruction is essentially not removed by mechanical means (for example, by physically removing the obstruction as described in the transient stroke models described above) or by chemical means (such as removal of a thrombus or embolus using a thrombolytic agent; see, e.g., Bowes et al., Neurology 45:815-819 (1995)) prior to a therapeutic benefit achieved by administration of the CD18 or CD11b antagonist (i.e., the increase in cerebral blood flow and/or the reduction in infarct size). However, this term would encompass situations wherein the arterial obstruction is slightly reduced in size as a consequence of endogenous thrombolytic molecules dissolving part of the thrombus/embolus, provided that at least some (e.g., about 50% and preferably about 80%) of the arterial obstruction remains intact following any such size reduction.

By "increasing cerebral blood flow or reducing infarct size" is meant the act of improving clinical outcome by inducing a statistically or physiologically significant increase in cerebral blood flow and/or a statistically or physiologically significant reduction in infarct size in a treated mammal relative to an untreated mammal as determined using techniques which are well known in the art, such as vascular imaging, for example. Preferably cerebral blood flow as determined 2-4 hours after administration of the antagonist is increased by at least 30% and preferably at least 50% relative to an untreated mammal. Desirably, infarct size measured 48 hours after administration of the antagonist will be 20% less and preferably 50% less than that of an untreated mammal.

The term "CD18 antagonist" when used herein refers to a molecule which binds to CD18 (preferably human CD18) and inhibits or substantially reduces a biological activity of CD18. Normally, the antagonist will block (partially or completely) the ability of a cell (e.g. a neutrophil) expressing the CD18 subunit at its cell surface to bind to endothelium. Non-limiting examples of CD18 antagonists include antibodies, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. In the preferred embodiment of the invention, the CD18 antagonist is an antibody.

Examples of anti-CD18 antibodies include MHM23 (Hildreth et al., Eur. J. Immunol. 13:202-208 (1983)); M18/2 ($IgG_{2a}$; Sanches-Madrid et al., J. Exp. Med. 158:586 (1983)); H52 (American Type Culture Collection (ATCC) Deposit HB10160); Mas191c and IOT18 (Vermot Desroches et al., Scand. J. Immunol. 33:277-286 (1991)); and NA-8 (WO 94/12214). The preferred antibody is one which binds to the CD18 epitope to which either MHM23 or H52 binds. Preferably the antibody has a high affinity for the CD18 polypeptide. In preferred embodiments, the antibody has an affinity for the CD18 antigen of about 4 nM or less. Preferably, the affinity is about 3 nM or less, and most preferably 1 nM or less. In certain embodiments, the antibody may bind to a region in the extracellular domain of CD18 which associates with CD11b and the antibody may also dissociate $\alpha$ and $\beta$ chains (e.g. the antibody may dissociate the CD11b and CD18 complex as is the case for the MHM23 antibody).

The term "CD11b antagonist" when used herein refers to a molecule which binds to CD11b and inhibits or substantially reduces a biological activity of CD11b. Normally, the antagonist will block (partially or completely) the ability of a cell (e.g. a neutrophil) expressing the CD11b subunit at its cell surface to bind to endothelium. Non-limiting examples of CD11b antagonists include antibodies, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. The preferred CD11b antagonist is an antibody, especially an anti-CD11b antibody which binds human CD11b. Exemplary CD11b antibodies include MY904 (U.S. Pat. No. 4,840,793); 1B6c (see Zhang et al., *Brain Research* 698:79-85 (1995)); CBRN1/5 and CBRM1/19 (WO94/08620).

The term "antibody" is used in the broadest sense and specifically covers monoclonal antibodies, antibody compositions with polyepitopic specificity, bispecific antibodies, diabodies, and single-chain molecules, as well as antibody fragments (e.g., Fab, F(ab')$_2$, and Fv), so long as they antagonize the biological activity of CD11b or CD18.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonaly antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature*, 321:522-525 (1986); Reichmann et al., *Nature*, 332:323-329 (1988); and Presta, *Curr. Op. Struct. Biol.*, 2:593-596 (1992). The humanized antibody includes a Primatized™ antibody wherein the antigen-binding region of the antibody is derived from an antibody produced by immunizing macaque monkeys with the antigen of interest.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun In *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains oh the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90: 6444-6448 (1993).

As used herein, the term "salvage receptor binding epitope" refers to an epitope of the Fc region of an IgG molecule (e.g., IgG$_1$, IgG$_2$, IgG$_3$, and IgG$_4$) that is responsible for increasing the in vivo serum half-life of the IgG molecule.

"Treatment" refers to both therapeutic treatment and prophylactic or preventative measures. Those in need of treatment include those already with the disorder as well as those in which the disorder is to be prevented. This application is mostly concerned with treating those individuals who have been diagnosed as having suffered acute ischemic stroke.

"Mammal" for purposes of treatment refers to any animal classified as a mammal, including humans, domestic and farm animals, and zoo, sports, or pet animals, such as dogs, horses, cats, cows, etc. Preferably, the mammal is human.

A "thrombolytic agent" is a molecule which breaks up or dissolves a thrombus. Exemplary thrombolytic agents include streptokinase, acylated plasminogen-streptokinase activator complex (APSAC), urokinase, single-chain urokinase-plasminogen activator (scu-PA), thrombin like enzymes from snake venoms such as ancrod (Bell, W. "Defribinogenating enzymes" In Colman et al., (eds): *Hemostasis and Thrombosis* Lippincott, Philadelphia (1987) p. 886), tissue plasminogen activator (t-PA) and biologically active variants of each of the above. The preferred thrombolytic agent is t-PA.

In the context of the present invention, the terms "tissue plasminogen activator" and "t-PA" are used interchangeably and denote extrinsic (tissue type) plasminogen activator having at least two functional domains consisting of a protease domain that is capable of converting plasminogen to plasmin and an N-terminal region believed to be responsible for fibrin binding. These terms therefore include polypeptides containing these functional domains as part of the overall amino acid sequence, irrespective of their source and method of preparation (e.g. these terms cover vampire bat t-PAs as disclosed in EP 352,119). The terms "human tissue plasminogen activator" and "human t-PA" are used interchangeably and denote wild-type human tissue plasminogen activator and functional derivatives thereof. Examples of t-PA functional derivatives include those molecules with extended half-life and improved fibrin specificity as disclosed in WO 93/24635; N-terminally truncated t-PA variants (see EP 382,174); and C84S t-PA described in Suzuki et al. *J. Cardiovasc. Pharmacol.* 22:834-840 (1993), for example.

II. Modes for Carrying Out the Invention

The invention provides a method for treating focal ischemic stroke, such as thromboembolic stroke. In particular, cerebral blood flow can be increased and/or infarct size can be reduced in focal ischemic stroke by administering an effective amount of a CD11b and/or CD18 antagonist to the mammal having suffered the stroke. In this method, the arterial obstruction is not removed prior to observation of the therapeutic benefit as defined herein, and as such the method does not require prior administration of a thrombolytic agent to the mammal in order to remove an embolus/thrombus and thereby increase cerebral blood flow and/or reduce infarct size.

It is contemplated that the CD18 or CD11a antagonist of the present invention will be administered to a patient as soon as possible once the condition of acute ischemic stroke has been diagnosed or is suggested by focal deficit on neurologic examination. Neurologic examination and, optionally, neuroimaging techniques such as computed tomography (CT) and magnetic resonance imaging (MRI) (including diffusion weighted imaging (DWI) and perfusion imaging (PI)); vascular imaging (e.g., duplex scanning and transcranial Doppler ultrasound and laser Doppler); angiography (e.g., computerized digital subtraction angiography (DSA) and MR angiography) as well as other invasive or non-invasive techniques are available for the diagnosis of acute ischemic stroke.

Preferably, the CD18 or CD11a antagonist will be administered at least once or continuously at any time from immediately following to about 24 hours after the onset of stroke. In certain embodiments, the CD18 or CD11a antagonist is first administered to the patient at a time between about 15 minutes (or 30 minutes or 45 minutes) to about 5 hours (or 12 hours or 24 hours) from the onset of stroke. For example, the antagonist may be first administered by bolus dosage as soon as stroke is diagnosed, followed by a subsequent bolus dosage of the antagonist (e.g. 5-24 hours after the initial bolus dosage).

The preferred antagonist for use in the above method is humanized H52 antibody (huH52), especially the huH52 F(ab')$_2$ antibody fragment.

The sequence of the heavy chain of the huH52 Fab is:

(SEQ ID NO: 10)
EVQLVESGGGLVQPGGSLRLSCATSGYTFTEYTMHWMRQAPGKGLEWVAG

INPKNGGTSHNQRFMDRFTISVDKSTSTAYMQMNSLRAEDTAVYYCARWR

GLNYGFDVRYFDVWGQGTLVTVSSASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSCDKTHT.

The sequence of the light chain of the huH52 Fab is:

(SEQ ID NO: 11)
DIQMTQSPSSLSASVGDRVTITCRASQDINNYLNWYQQKPGKAPKLLIYY

TSTLHSGVPSRFSGSGSGTDYTLTISSLQPEDFATYYCQQGNTLPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

In other embodiments, the full length IgG$_2$ huH52 antibody may be the molecule of choice. The heavy chain of the full length IgG$_2$ huH52 antibody has the sequence:

(SEQ ID NO: 12)
EVQLVESGGGLVQPGGSLRLSCATSGYTFTEYTMHWMRQAPGKGLEWVAG

INPKNGGTSHNQRFMDRFTISVDKSTSTAYMQMNSLRAEDTAVYYCARWR

GLNYGFDVRYFDVWGQGTLVTVSSASTKGPSVFPLAPCSRSTSESTAALGC

LVKDYFPEPVTVSWNSGALTSGVHTFPAVLQSSGLYSLSSVVTVTSSNFG

TQTYTCNVDHKPSNTKVDKTVERKCCVECPPCPAPPVAGPSVFLFPPKPK

DTLMISRTPEVTCVVVDVSHEDPEVQFNWYVDGMEVHNAKTKPREEQFNS

TFRVVSVLTVVHQDWLNGKEYKCKVSNKGLPAPIEKTISKTKGQPREPQV

YTLPPSREEMTKNQVSLTCLVKGFYPSDIAVEWESNGQPENNYKTTPPML

DSDGSFFLYSKLTVDKSRWQQGNVFSCSVMHEALHNHYTQKSLSLSPGK.

The light chain of the full length IgG$_2$ huH52 antibody has the sequence:

(SEQ ID NO: 11)
DIQMTQSPSSLSASVGDRVTITCRASQDINNYLNWYQQKPGKAPKLLIYY

TSTLHSGVPSRFSGSGSGTDYTLTISSLQPEDFATYYCQQGNTLPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

A description follows as to the production of the preferred antagonists (i.e. antibodies), long half-life antagonists, pharmaceutical formulations, modes for administration, as well as kits and articles of manufacture for use in the claimed methods. The description in relation to long half-life antagonists, pharmaceutical formulations and modes for administration is also relevant to the use of thrombolytic agents in certain embodiments of the invention.

A. Antibody Preparation

According to the preferred embodiment of the invention, the CD18 or CD11b antagonist is an antibody. Various antibodies which bind to CD18 and CD11 bare available in the art. Furthermore, a description follows as to the production of anti-CD18 or anti-CD11b antibodies for use in the treatment of stroke as defined herein.

(i) Polyclonal Antibodies.

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups.

Animals are immunized against the antigen, immunogenic conjugates, or derivatives by combining 1 mg or 1 μg of the peptide or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130:151-188 (1992).

In a further embodiment, antibodies or antibody fragments can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567 (Morrison, et al., *Proc. Natl Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

(iii) Humanized and Human Antibodies.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567, wherein substantially less than an intact human variable domain has been substituted by the corresponding sequence from a non-human species. In practice, humanized antibodies are typically human antibodies in which some. CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immunol.*, 7:33 (1993). Human antibodies can also be derived from phage-display libraries (Hoogenboom et al., *J. Mol. Biol.*, 227:381 (1991); Marks et al., *J. Mol. Biol.*, 222:581-597 (1991)).

(iv) Bispecific Antibodies

Bispecific antibodies (BsAbs) are antibodies that have binding specificities for at least two different epitopes. Exemplary BsAbs may bind to two different epitopes of the CD18 antigen or may bind both CD18 and CD11b. Such antibodies can be derived from full length antibodies or antibody fragments (e.g. F(ab')$_2$ bispecific antibodies).

Methods for making bispecific antibodies are known in the art. Traditional production of full length bispecific antibodies is based on the coexpression of two Immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published 13 May 1993, and in Traunecker et al., *EMBO J.*, 10:3655-3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies see, for example, Suresh et al., *Methods in Enzymology,* 121:210 (1986). Using such techniques, a bispecific molecule which combines a thrombolytic agent such as t-PA and an anti-CD18 or anti-CD11b antibody can be prepared for use in the treatment of stroke as defined herein.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. The following techniques can also be used for the production of bivalent antibody fragments which are not necessarily bispecific. For example, Fab' fragments recovered from *E. coli* can be chemically coupled in vitro to form bivalent antibodies. See, Shalaby et al., *J. Exp. Med.,* 175:217-225 (1992).

Various techniques for making and isolating bivalent antibody fragments directly from recombinant cell culture have also been described. For example, bivalent heterodimers have been produced using leucine zippers. Kostelny et al., *J. Immunol.,* 148(5):1547-1553 (1992). The leucine zipper peptides from the Fos and Jun proteins were linked to the Fab' portions of two different antibodies by gene fusion. The antibody homodimers were reduced at the hinge region to form monomers and then reoxidized to form the antibody heterodimers. The "diabody" technology described by Hollinger et al., *Proc. Natl. Acad. Sci. USA,* 90:6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (sFv) dimers has also been reported. See Gruber et al., *J. Immunol.,* 152:5368 (1994).

B. Long Half-life Antagonists

In certain embodiments of the invention, it is desirable to use CD18 or CD11b antagonists engineered to have an enhanced half-life in the serum of a mammal treated therewith. For example, this may be achieved by (i) incorporating a salvage receptor binding epitope of the Fc region of an IgG into the antagonist so as to increase its circulatory half-life, but without disrupting its biological activity or (ii) covalently binding a nonproteinaceous polymer to the antagonist. These exemplary techniques will be described briefly below:

(i) Antagonist-salvage Receptor Binding Epitope Fusions.

Incorporation of a salvage receptor binding epitope into the antagonist can take place by any means, such as by mutation of the appropriate region in the antagonist of interest to mimic the Fc region or by incorporating the epitope into a peptide tag that is then fused to the antagonist at either end or in the middle or by DNA or peptide synthesis.

A systematic method for preparing such an antagonist variant having an increased in vivo half-life comprises several steps. The first involves identifying the sequence and conformation of a salvage receptor binding epitope of an Fc region of an IgG molecule. Once this epitope is identified, the sequence of the antagonist of interest is modified to include the sequence and conformation of the identified binding epitope. After the sequence is mutated, the antagonist variant is tested to see if it has a longer in vivo half-life than that of the original antagonist. If the antagonist variant does not have a longer in vivo half-life upon testing, its sequence is further altered to include the sequence and conformation of the identified binding epitope. The altered antagonist is tested for longer in vivo half-life, and this process is continued until a molecule is obtained that exhibits a longer in vivo half-life.

The salvage receptor binding epitope being thus incorporated into the antagonist of interest is any suitable such epitope as defined above, and its nature will depend, e.g., on the type of antagonist being modified. The transfer is made such that the antagonist of interest is still able to antagonize the biological activity of CD11b or CD18.

Where the antagonist of interest is an antibody, it contains an Ig domain or Ig-like domain and the salvage receptor binding epitope is placed so that it is located within this Ig domain or Ig-like domain. More preferably, the epitope constitutes a region wherein any one or more amino acid residues from one or two loops of the Fc domain are transferred to an analogous position of the Ig domain or Ig-like domain of the antibody. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of an Ig or to a Ig-like domain. Alternatively, the epitope is taken from the CH2 domain of the Fc region and transferred to the $C_L$ region or $V_L$ region, or both, of an Ig or to an Ig-like domain of the antagonist of interest.

For example, for purposes of discussing variants wherein the polypeptide of interest is an antibody, reference is made to FIGS. 4A-B, which illustrates the relevant consensus primary structures of various Igs, i.e., human IgG$_1$ CH1 domain, human IgG$_2$ CH1 domain, human IgG$_3$ CH1 domain, human IgG$_4$ CH1 domain, human κC$_L$ domain, and human λC$_L$ domain, as well as the specific sequence for Fabv1b, a preferred anti-CD18 Fab variant herein. Further, FIGS. 4A-B indicates the residues of Fabv1b that are of interest and of most importance. In a preferred embodiment, the residues of importance are those with an asterisk in FIGS. 4A-B, i.e., in one loop of Fabv1b, MIS with a T residue one amino acid C-terminal to MIS, and in another loop of Fabv1b, HQN with a D residue two amino acids C-terminal to HQN and a K residue one amino acid C-terminal to the D residue.

In one most preferred embodiment, the salvage receptor binding epitope comprises the sequence (5' to 3'): PKNSSMISNTP (SEQ ID NO:8), and optionally further comprises a sequence selected from the group consisting of HQSLGTQ (SEQ ID NO: 13), HQNLSDGK (SEQ ID NO:9), HQNIS-DGK (SEQ ID NO:14), or VISSHLGQ (SEQ ID NO:15), particularly where the antagonist of interest is a Fab or F(ab')$_2$.

(ii) Antagonist-polymer Conjugates.

The nonproteinaceous polymer of choice for this purpose is ordinarily is a hydrophilic synthetic polymer, i.e., a polymer not otherwise found in nature. However, polymers which exist in nature and are produced by recombinant or in vitro methods are useful, as are polymers which are isolated from native sources. Hydrophilic polyvinyl polymers fall within the scope of this invention, e.g. polyvinylalcohol and polyvinylpyrrolidone. Particularly useful are polyalkylene ethers such as polyethylene glycol (PEG); polyelkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galaptosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon. The polymer prior to cross-linking need not be, but preferably is, water soluble, but the final conjugate must be water soluble. In addition, the polymer should not be highly immunogenic in the conjugate form, nor should it possess viscosity that is incompatible with intravenous infusion or injection if it is intended to be administered by such routes.

Preferably the polymer contains only a single group which is reactive. This helps to avoid cross-linking of protein molecules. However, it is within the scope herein to optimize reaction conditions to reduce cross-linking, or to purify the reaction products through gel filtration or chromatographic sieves to recover substantially homogeneous derivatives.

The molecular weight of the polymer may desirably range from about 100 to 500,000, and preferably is from about 1,000 to 20,000. The molecular weight chosen will depend upon the nature of the polymer and the degree of substitution. In general, the greater the hydrophilicity of the polymer and the greater the degree of substitution, the lower the molecular weight that can be employed. Optimal molecular weights will be determined by routine experimentation.

The polymer generally is covalently linked to the antagonist though a multifunctional crosslinking agent which reacts with the polymer and one or more amino acid or sugar residues of the antagonist to be linked. However, it is within the scope of the invention to directly crosslink the polymer by reacting a derivatized polymer with the hybrid, or vice versa.

Covalent binding to amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, succinimidyl active esters, activated dithiocarbonate PEG, 2,4,5-trichlorophenylcloroformate or P-nitrophenylcloroformate activated PEG). Carboxyl groups are derivatized by coupling PEG-amine using carbodiimide.

Polymers are conjugated to oligosaccharide groups by oxidation using chemicals, e.g. metaperiodate, or enzymes, e.g. glucose or galactose oxidase, (either of which produces the aldehyde derivative of the carbohydrate), followed by reaction with hydrazide or amino derivatized polymers, in the same fashion as is described by Heitzmann et al., *Proc. Natl. Acad. Sci. USA* 71:3537-41 (1974) or Bayer et al., *Methods in Enzymology* 62:310 (1979), for the labeling of oligosaccharides with biotin or avidin. Further, other chemical or enzymatic methods which have been used heretofore to link oligosaccharides are particularly advantageous because, in general, there are fewer substitutions than amino acid sites for derivatization, and the oligosaccharide products thus will be more homogenous. The oligosaccharide substituents also are optionally modified by enzyme digestion to remove sugars, e.g. by neuraminidase digestion, prior to polymer derivatization.

The polymer will bear a group which is directly reactive with an amino acid side chain, or the N- or C-terminus of the antagonist linked, or which is reactive with the multifunctional cross-linking agent. In general, polymers bearing such reactive groups are known for the preparation of immobilized proteins. In order to use such chemistries here, one should employ a water soluble polymer otherwise derivatized in the same fashion as insoluble polymers heretofore employed for protein immobilization. Cyanogen bromide activation is a particularly useful procedure to employ in crosslinking polysaccharides.

"Water soluble" in reference to the starting polymer means that the polymer or its reactive intermediate used for conjugation is sufficiently water soluble to participate in a derivatization reaction. "Water soluble" in reference to the polymer conjugate means that the conjugate is soluble in physiological fluids such as blood.

The degree of substitution with such a polymer will vary depending upon the number of reactive sites on the antagonist, whether all or a fragment of the antagonist is used, whether the antagonist is a fusion with a heterologous protein (e.g. anti-CD18 antibody fused to a salvage receptor binding epitope), the molecular weight, hydrophilicity and other characteristics of the polymer, and the particular antagonist derivatization sites chosen. In general, the conjugate contains about from 1 to 10 polymer molecules, while any heterologous sequence may be substituted with an essentially unlimited number of polymer molecules so long as the desired activity is not significantly adversely affected. The optimal degree of cross-linking is easily determined by an experimental matrix in which the time, temperature and other reaction conditions are varied to change the degree of substitution, after which the ability of the conjugates to function in the desired fashion is determined.

The polymer, e.g. PEG, is cross-linked by a wide variety of methods known per se for the covalent modification of proteins with nonproteinaceous polymers such as PEG.

The long half-life conjugates of this invention are separated from the unreacted starting materials by gel filtration. Heterologous species of the conjugates are purified from one another in the same fashion. The polymer also may be water-insoluble, as a hydrophilic gel.

C. Pharmaceutical Formulations

Therapeutic formulations of the CD11b or CD18 antagonist are prepared for storage by mixing the antagonist having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; amino acids such as glycine, glutamine, asparagine, histidine, arginine or lysine; monosaccharides, disaccharides and other carbohydrates including glucose, mannose, trehalose or dextrins; chelating agents such as EDTA; sugar alcohols such as mannitol or sorbitol; salt-forming counterions such as sodium; and/or nonionic surfactants such as Tween, Pluronics or PEG.

The active ingredients may also be entrapped in microcapsules prepared, for example, by coacervation techniques or by interfacial polymerization, for example, hydroxymethylcellulose or gelatin-microcapsules and poly-(methylmethacylate)microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes, prior to or following lyophilization and reconstitution.

Sustained-release preparations may be prepared. Suitable examples of sustained-release preparations include semipermeable matrices of solid hydrophobic polymers containing the CD18 or CD11b antagonist, which matrices are in the form of shaped articles, e.g. films, or microcapsules Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release CD18 or CD11b antagonist compositions also include liposomally entrapped antagonists. Liposomes containing the CD18 or CD11b antagonist are prepared by methods known in the art, such as described in Epstein et al., *Proc. Natl. Acad. Sci. USA*, 82:3688 (1985); Hwang et al., *Proc. Natl Acad. Sci. USA*, 77:4030 (1980); and U.S. Pat. Nos. 4,485,045 and 4,544,545. Ordinarily, the liposomes are the small (about 200-800 Angstroms) unilamelar type in which the lipid content is greater than about 30 mol. % cholesterol, the selected proportion being adjusted for the optimal CD18 or CD116 antagonist therapy. Liposomes with enhanced circulation time are disclosed in U.S. Pat. No. 5,013,556.

D. Modes for Administration

The CD18 or CD11b antagonists of the invention are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of the antagonist is preferred.

The appropriate dosage of CD18 or CD11b antagonist will depend on the nature of the stroke to be treated, the severity and course of the stroke, whether the antagonist is administered for preventive or therapeutic purposes, previous therapy, the patient's clinical history and response to the CD18 or CD11b antagonist, and the discretion of the attending physician. The CD18 or CD11b antagonist is suitably administered to the patient at one time or over a series of treatments and may be administered to the patient at any time from diagnosis onwards. For example, the antagonist may be administered at a time between about 15, 30 or 45 minutes to about 5 hours, 12 hours or 24 hours from the onset of stroke. In preferred embodiments, the initial dose is followed by at least one subsequent dose (e.g., from 5 to 24 hours after the initial dose). In certain situations, CD11b antagonist and CD18 antagonist are co-administered to the mammal.

Where the antagonist is an antibody, from about 100 μg/kg to about 20 mg/kg, and preferably from about 500 μg/kg to about 5 mg/kg, and most preferably from about 1 mg/kg to about 3 mg/kg of the anti-CD18 or anti-CD11b antibody is an initial candidate dosage for administration to the patient, whether, for example, by one or more separate administrations, or by continuous infusion. However, other dosage regimens may be useful. The progress of this therapy is easily monitored by conventional techniques and assays elaborated herein.

E. Kits and Articles of Manufacture

In another embodiment of the invention, there are provided articles of manufacture and kits containing materials useful for improving clinical outcome in stroke by increasing cerebral blood flow and/or reducing infarct size. The article of manufacture comprises a container with a label. Suitable containers include, for example, bottles, vials, and test tubes. The containers may be formed from a variety of materials such as glass or plastic. The container holds a composition which is effective for treating stroke as defined herein and may have a sterile access port (for example the container may be an intravenous solution bag or a vial having a stopper pierceable by a hypodermic injection needle). The active agent in the composition is a CD11b or CD18 antagonist. The label on the container indicates that the composition is used for treating stroke as described above, and may also indicate directions for in vivo use, such as those described above.

The kit of the invention comprises the container described above and a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The following examples are offered by way of illustration and not by way of limitation. The disclosures of all citations in the specification are expressly incorporated herein by reference.

EXAMPLE

This study investigated the effect of anti-CD18 antibody (MHM23) and t-PA in a rabbit model of thromboembolic stroke. In this model, a single blood clot is introduced into the middle cerebral and posterior communicating arteries (which are "main cerebral arteries"). The arterial obstruction (i.e., the clot) remains in place throughout the experiment (unless it is enzymatically removed by t-PA). The following rabbit model is thought to correlate well with the physiological progression of thromboembolic stroke in humans.

Materials and Methods

The rabbit model of thromboembolic stroke used in the current study has been previously described in detail (Bednar et al., *Neurol. Res.*, 16:129-132 (1994); Gross et al., *Stroke*, 24:558-562 (1993); Kohut et al., *Stroke*, 23:9397 (1992); Wilson et al., *Neurosurgery*, 31:929-934 (1992)). See, also, Gross et al., *Neurosurgery*, 36(6):1172-1177 (1995).

Briefly, New Zealand white rabbits (Charles River, Calif.) (both males and females; 3.0-3.5 kg) were anesthetized with the solution of ketamine (50 mg/kg; Aveco Co., Fort Dodge, Iowa), acepromazine (20 mg, Aveco Co.), and xylazine (5 mg/kg; Mobay Corp., Shawnee, Kans.), a solution that was subsequently used to maintain sufficient anesthesia for painless surgery (as determined by responses to various physiological and autonomic stimuli, including mean arterial pressure and response to a paw being pinched). After an incision was made in the right femoral triangle to expose the femoral vein and artery, the femoral artery was cannulated with a PE-90 catheter (BD Co., Parsippany, N.J.), to which was attached a platinum-iridium electrode. This catheter-electrode permitted the continuous measuring of mean arterial pressure and blood sampling for measurement of arterial blood gases (ABG) (pH, $PCO_2$, $PO_2$), hematocrit, and glucose and for determination of hydrogen washout to assess the rCBF by the hydrogen clearance technique (Young, *Stroke*, 11:552-564 (1980)). After the femoral vein was cannulated with PE-90 tubing for drug infusions, a midline scalp incision was made to expose the calvarium. Bilateral craniectomies were performed and the following were placed; 30-gauge platinum-iridium electrodes to monitor the regional cerebral blood flow (rCBF); a fiberoptic, epidural intracranial pressure (ICP) monitor (Princeton Medical Corp., Hudson, N.H.); and a temperature sensor (Yellow Springs Instruments, Yellow Springs, Ohio) to measure brain temperature. All cranial instrumentation was carefully fixed in place with fast-setting epoxy. Through a midline neck incision, the animal was tracheostomized and mechanically ventilated. Both depth and rate of ventilation were modified as needed to maintain ABGs within physiological range.

Throughout the experiment, the brain and core temperatures, mean arterial pressure, and ICP were continuously measured. Additionally, the following parameters were measured before embolization (baseline), at the time of embolization, and hourly after embolization; the rCBF, hematocrit, glucose, and ABG. The mean arterial pressures were kept between 50 and 60 mm Hg throughout the experiment. Fluids (Ringer's lactate or packed cells) were given intravenously as needed (approximately 2-4 ml/kg/h) to maintain euvolemia. Core and brain temperatures were maintained within 1° C. of baseline by using heating blankets and heating lamps.

The autologous clot was prepared by mixing the whole blood (1 ml) with 50 mg of tin granules. The clot was introduced into the PE-90 tubing pretreated with thrombin and was allowed to mature at room temperature.

After tracheostomy, the region of the bifurcation of the common carotid artery was identified, followed by 30 to 60 minutes of equilibration, during which baseline values were obtained. All surgery was completed within 2 hours. Once all the baseline values were obtained, the proximal internal carotid artery and the distal common carotid artery were transiently isolated from the circulation. An arteriotomy was then performed, and the autologous clot embolus was delivered to the anterior circulation of the brain via a catheter advanced into the proximal internal carotid artery. Once embolized, both the proximal internal carotid artery and distal common carotid artery were again isolated from the circulation and an arteriorrhaphy was performed by using 10-0 interrupted nylon sutures. A Philip's dental x-ray machine was used to obtain a submental-vertex radiograph that verified placement of the tin-tagged clot. Embolized clots were noted within the middle cerebral and posterior communicating arteries.

t-PA or a saline solution (0.9% saline) was administered intravenously by continuous infusion from hours 3-5 after the embolization at a total dose of 6.3 mg/kg. MHM23 (2 mg/kg) was administered by bolus dosage 1 hour after embolization. In each instance, the experiment continued for 7 hours after embolization. Submental-vertex radiographs were obtained after embolization and at the end of the experiment. Immediately after the embolization, the rCBF was measured again; the experiment was continued if the rCBF was $\leq 15$ ml/100 g/min in any of the three electrodes in the embolized hemisphere (Jones et al., *J. Neurosurg.*, 54:773-782 (1981)).

At the end of the experiment, the animals were killed with an overdose of sodium pentobarbital (150 mg/kg), a procedure recognized as acceptable and painless, according to the euthanasia guidelines of the American Veterinary Medical Association. Bilateral thoracotomies were performed in accordance with procedures outlined by the University of Vermont Institutional Animal Care and Utilization Committee. The brain was harvested rapidly and examined grossly for the presence and position of residual clot. The brain was cut into 2-mm slices in a bread-loaf fashion and incubated in triphenyltetrazolium chloride dye to define the size of the brain infarct (Bose et al., *Stroke*, 19:28-37 (1988)). This method has been shown to be an acceptable means of determining the size of a brain infarct in our rabbit model and correlates well with hematoxylin and eosin staining (Bednar et al., *Neurol. Res.*, 16:129-132 (1994)). Each brain slice was carefully traced onto clear acetate sheets for later planimetric determination of the infarct size, for which an IBM image analyzer was used. The infarct size was determined according to the modification described by Lin et al., *Stroke*, 24:117-121 (1993). In this method, the region of the infarct is determined by subtracting the volume of the noninfarcted part of the embolized hemisphere from the entire volume of the nonembolized hemisphere. This modification takes into account that the volume of a brain infarct may be overestimated because of associated swelling.

The analysis of variance for repeated measures was used to analyze the hematocrit, glucose, ABG, rCBF, and ICP in the control and treated groups. If significance was noted, the values of these variables immediately before the t-PA and/or MHM23 administration were then compared by the Student's t test. When necessary, the analysis of covariance was used to compare the control and treated groups. After a significant treatment-by-time interaction, individual contrasts were used to compare the treatment means at each time point; that is, if a significant treatment-by-time interaction was noted, the treatment effects were examined at each time point. The infarct size and specific gravities of the brain were compared (treated versus control) by the Student's t test. All the results were two-sided and were evaluated by using $\alpha = 0.05$.

Results

Figure 2:
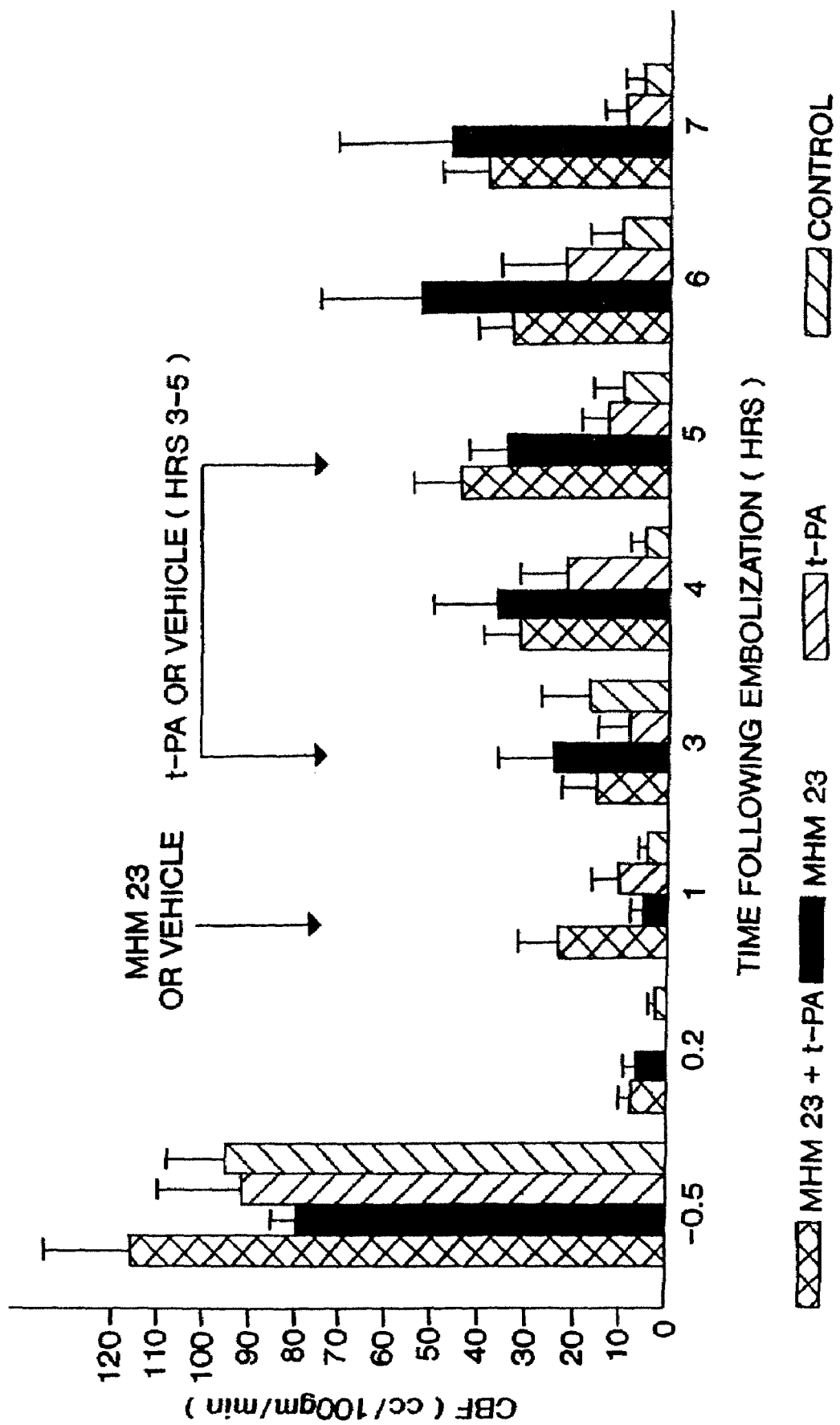
FIG. 2 depicts regional cerebral blood flow (CBF; cc/100 gm/min) over time in embolized rabbits following treatment with MHM23 (anti-CD18) and t-PA (n=5); MHM23 alone (n=5); t-PA alone (n=10) or saline solution control (n=10) as described in Example 1. MHM23 or saline solution control was administered 1 hour following embolization. t-PA or saline solution control was administered by continuous infusion over hours 3-5 following embolization (mean+/−standard error of the mean).
Figure 3:
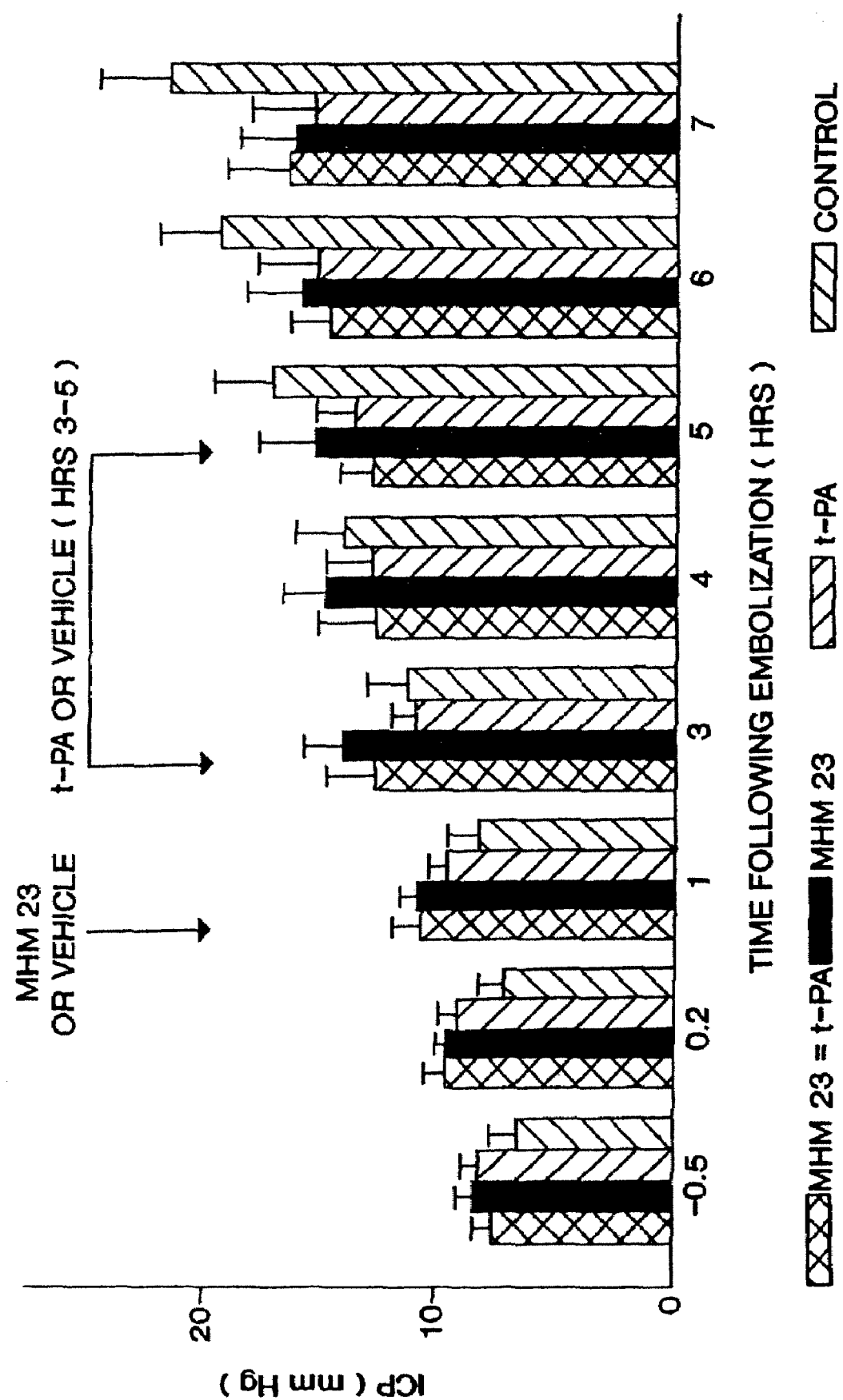
FIG. 3 illustrates intracranial pressure (ICP; mm Hg) in embolized rabbits following treatment with MHM23 (anti-CD18) and t-PA (n=5); MHM23 alone (n=5); t-PA alone (n=10) or saline solution control (n=10) as described in Example 1. MHM23 or saline solution control was administered 1 hour following embolization. t-PA or saline solution control was administered by continuous infusion over hours 3-5 following embolization (mean+/−standard error of the mean).

The results of the above experiment are depicted in FIGS. 1-3. As shown in FIGS. 1 and 2, administration of anti-CD18 antibody alone, lead to a significant increase in cerebral blood flow as well as a significant reduction in infarct size relative to control. FIG. 3 shows that anti-CD18 antibody alone, t-PA alone, or a combination of these two agents tend to reduce intracranial pressure (ICP) at 6-7 hours. Furthermore, the experiments show that anti-CD18 antibody is compatable with t-PA and improves the outcome of t-PA when given at 3-5 hours after installation of the clot into the cerebral circulation.

The increase in cerebral blood flow and the reduction in infarct size observed in the above experiments are thought to be predictive of an improvement in clinical outcome as measured by a standard stroke scale. Accordingly, this application provides a method for improving clinical outcome in patients having suffered stroke as defined herein.

The model described in this example differs from that previously described in Bednar et al., Stroke 23(1):152 (1992) in that the animals in the study were not subjected to extraneous systemic hypotension (by reducing the mean arterial pressure in the animal to 30 mmHg by controlled exsanguination). Also, the anti-CD18 antibody was given more than 30 minutes after the thromboembolic event and the dose was different.

---

The invention claimed is:

1. A method for increasing cerebral blood flow and/or reducing infarct size in focal ischemic stroke caused by obstruction of a main cerebral artery in a human mammal which comprises the step of co-administering effective amounts of tissue plasminogen activator (tPA), anti-CD11b antibody, and anti-CD18 antibody to the mammal wherein neither the tPA nor the anti-CD18 antibody is administered to the mammal until about three to five hours after the onset of focal ischemic stroke.

2. The method of claim 1 that increases cerebral blood flow and reduces infarct size in the mammal.

3. The method of claim 1 wherein the anti-CD11b antibody is an antibody fragment.

4. The method of claim 3 wherein the anti-CD11b antibody fragment is a F(ab')$_2$.

5. The method of claim 1 wherein the anti-CD11b antibody is humanized.

6. The method of claim 1 wherein the anti-CD11b antibody is administered to the mammal by bolus dosage.

7. The method of claim 1 wherein the anti-CD11b antibody is administered intravenously.

8. The method of claim 1 wherein the anti-CD11b antibody is administered via continuous infusion.

9. The method of claim 1 wherein the anti-CD11b antibody and the tPA are simultaneously administered to the mammal.

10. The method of claim 1 wherein the anti-CD11b antibody is administered before the tPA is administered to the mammal.

11. The method of claim 1 wherein the anti-CD11b antibody is a humanized anti-CD11b antibody.

12. The method of claim 11 wherein the humanized anti-CD11b antibody is a F(ab')$_2$.

13. The method of claim 1, wherein the anti-CD18 antibody binds to an extracellular domain of CD18 and inhibits or reduces the ability of a cell expressing CD18 to bind to endothelium.

14. The method of claim 1, wherein the anti-CD18 antibody binds CD18 with an affinity of 4 nM or less.

15. The method of claim 1, wherein the anti-CD18 antibody binds CD18 with an affinity of 3 nM or less.

16. The method of claim 1, wherein the anti-CD18 antibody binds CD18 with an affinity of 1 nM or less.

17. The method of claim 1, wherein the anti-CD18 antibody dissociates the CD11b/CD18 complex.

18. The method of claim 1, wherein the anti-CD18 antibody is a humanized H52 antibody comprising a heavy chain sequence of SEQ ID NO:10 or SEQ ID NO: 12 and comprising a light chain sequence of SEQ ID NO: 11.

* * * * *

UNITED STATES PATENT AND TRADEMARK OFFICE
CERTIFICATE OF CORRECTION

PATENT NO. : 7,655,230 B2  
APPLICATION NO. : 12/107050  
DATED : February 2, 2010  
INVENTOR(S) : Bednar et al.

Page 1 of 1

It is certified that error appears in the above-identified patent and that said Letters Patent is hereby corrected as shown below:

Title Page Amend assignee:

(73) Assignee: Genentech, Inc., South San Francisco, CA (US) <u>and University of Vermont and State Agricultural College, Burlington, VT (US)</u>

Signed and Sealed this

Twenty-ninth Day of June, 2010

David J. Kappos
*Director of the United States Patent and Trademark Office*